US006299520B1

(12) United States Patent
Cheyne, III

(10) Patent No.: US 6,299,520 B1
(45) Date of Patent: Oct. 9, 2001

(54) ANTIMICROBIAL SCRUB PAD

(75) Inventor: Robert H. Cheyne, III, Cumberland, RI (US)

(73) Assignee: ACS Industries, Inc., Woonsocket, RI (US)

(*) Notice: Subject to any disclaimer, the term of this patent is extended or adjusted under 35 U.S.C. 154(b) by 0 days.

(21) Appl. No.: 09/413,918

(22) Filed: Oct. 7, 1999

Related U.S. Application Data

(63) Continuation-in-part of application No. 09/055,732, filed on Apr. 6, 1998, now abandoned.

(51) Int. Cl.$^7$ .................................................. B24D 3/34
(52) U.S. Cl. ......................................... 451/532; 451/536
(58) Field of Search ............................. 451/532, 536, 451/533, 537; 51/297, 298; 15/226, 209.1, 208

(56) References Cited

U.S. PATENT DOCUMENTS

| | | |
|---|---|---|
| 2,958,593 | * 11/1960 | Hoover et al. .................. 451/532 |
| 3,103,031 | 9/1963 | Winston . |
| 3,109,191 | 11/1963 | Cameron . |
| 3,261,675 | * 7/1966 | Cameron ......................... 451/532 |
| 3,280,517 | * 10/1966 | Copeland ........................ 451/536 |
| 3,324,609 | 6/1967 | Stein et al. . |
| 4,649,079 | 3/1987 | Guilbault et al. . |
| 4,715,150 | 12/1987 | Takeuchi et al. . |
| 4,781,974 | 11/1988 | Bouchette et al. . |
| 4,801,493 | 1/1989 | Ferziger et al. . |
| 5,152,809 | * 10/1992 | Mattesky ......................... 51/295 |
| 5,626,512 | * 5/1997 | Palaikis et al. ................. 451/536 |
| 5,856,002 | * 1/1999 | Mori ................................ 428/334 |
| 6,042,877 | 3/2000 | Lyon et al. . |

* cited by examiner

Primary Examiner—Robert Rose
(74) Attorney, Agent, or Firm—Hopgood, Calimafde, Judlowe & Mondolino LLP

(57) ABSTRACT

A nonabsorbent, abrasive scrubbing pad, especially for domestic use in the kitchen or bathroom, comprising a nonwoven web of fibers in which the fibers have coated thereon a mixture of antimicrobial compounds. The antimicrobial compounds are dispersed in a coating material that is applied to the fibers and then cured to anchor the antimicrobial compounds in the coating and prevent their being leached. The coating preferably also has dispersed therein abrasive particles to provide an abrasive scrubbing pad.

23 Claims, 2 Drawing Sheets

ANTIMICROBIAL SCRUB PAD

This application is a continuation-in-part of application Ser. No. 09/055,732, filed Apr. 6, 1998 now abandoned, the disclosure of which is incorporated herein by reference.

BACKGROUND OF THE INVENTION

1. Field of the Invention

The invention relates to nonwoven articles used for abrasively cleaning surfaces and having antimicrobial properties to prevent the growth of microbes in the nonwoven article during storage after having been used in a wet environment.

2. The State of the Art

Antimicrobial compounds have been used for decades in health care environments, such as in hospitals and physicians' offices, ever since Louis Pasteur's discovery of microbes as communicators of disease and infection. In the typical health care setting, different types of compounds are used to clean and disinfect different surfaces. These compounds can be as varied as the surfaces; everything from floors to tables to countertops made from plastics (e.g., melamine types) or metals (e.g., stainless steel) need to be cleaned.

More recently, antimicrobial compounds have been sold to consumers especially for cleaning kitchen and especially bathroom fixtures (e.g., toilets, sinks, bathtubs and showers). These formulations typically contain a quaternary ammonium compound optionally mixed with a surfactant, detergent, foaming agent, mild abrasive, and the like, and various combinations thereof. Still more recently, the transmission of infections microbes from raw food products, typically raw proteinaceous foodstuffs (typically chicken and beef), has heightened consumer awareness of microbial contamination and the need to cleanse and disinfect food preparation utensils and surfaces. Accordingly, the latest products have been liquid soaps containing an antimicrobial compound; these types of products were formerly available only in hospitals where soaps and surgical gowns had antibacterials incorporated therein. And still more recently childrens' toys, pacifiers, and various apparatus (e.g., playpens, bassinets, etc.) have been available with antibacterial properties so that microorganisms do not grow thereon. See, e.g., Stuart H. Levy, "The Challenge of Antibiotic Resistance," *Scientific American* (March 1998, p. 46–53).

Concomitant with consumer's awareness of becoming accidentally contaminated from bacteria living on food preparation surfaces, manufacturers and consumers came to realize that items such as sponges and towels (paper or cloth) that are used to clean such surfaces could be microbe-friendly environments because of their relatively high residual water content after use. Besides a food source and a tolerable temperature range, the other main requirement for bacterial growth is water. Sponges and towels absorb water and even when wrung and squeezed, may retain an amount of water sufficient to allow for bacterial growth in their interiors. For example, Roenigk, in U.S. Pat. No. 5,541,233 (the disclosure of which is incorporated herein by reference) describes the use of the combination of a chelating polymer and a metal complex for use in a water absorbing porous article (such as a sponge or towel). Others describe mixtures of compounds, such as a mixture of diazolidinyl urea and iodopropynyl butylcarbamate in T. Elder et al, in *Cosmetics and Toiletries*, v. 112, n. 8, p. 73 (1997), for use in personal care formulations.

Various types of abrasive cleaning pads have been devised. Winston, in U.S. Pat. No. 3,103,031, describes a non-woven scouring pad having a combination of synthetic fibers (e.g., urethane, epoxy, polyester) and metallic filaments interwoven. Cameron, in U.S. Pat. No. 3,109,191, describes a scouring article comprising a non-woven synthetic fiber bat bound with an adhesive and the fibers then plated with metal. Stein et al., in U.S. Pat. No. 3,324,609, describes an abrasive article having a non-woven web reinforced joined to a coextensive woven web; the non-woven web can be coated with an adhesive containing abrasive particles. Guilbault et al., in U.S. Pat. No. 4,649,079, teaches incorporating a hydrophobic, water in-insoluble biocide into a hydrophobic fiber by passing the fiber through a bath of the biocide. Other patent describing articles and fibers similar to these are described in the following U.S. Pat. No. 2,958,593 to Hoover et al.; U.S. Pat. No. 3,261,675 to Cameron; U.S. Pat. No. 3,280,517 to Copeland; U.S. Pat. No. 4,715,150 to Takeuchi et al.; U.S. Pat. No. 4,781,974 to Bouchette et al; and U.S. Pat. No. 4,801,493 to Ferziger et al.; U.S. Pat. No. 5,152,809 to Mattesky; U.S. Pat. No. 5,626,512 to Palaikis et al.; and U.S. Pat. No. 5,856,002 to Mori. The disclosures of all of these patents are incorporated herein by reference.

SUMMARY AND OBJECTS OF THE INVENTION

Among various objects of this invention are providing a new, durable, non-absorbent, scrubbing article in which the growth of microbes is deterred; the new scrubbing article is preferably abrasive, and is preferably provided as a flexible nonwoven pad. Another object of this invention is to provide such a pad that, to the extent possible, does not promote antimicrobial resistance.

In one embodiment, this invention provides a scrubbing pad comprising a nonwoven pad in which the fibers of which the pad is comprised have a coating comprising a combination of antimicrobial compounds. The antimicrobial compounds are preferably dispersed in a liquid material that is coated onto the fibers and then cured. The antimicrobial compounds thus are locked into the nonwoven pad and do not leach out to the surface being cleaned. The liquid material preferably has admixed therein an abrasive for the production of an abrasive, antimicrobial scrubbing article. In a particular embodiment, the antimicrobials are an antifungal and an antibacterial, especially one of the foregoing being an iodine-containing compound. Most preferably, the antimicrobials are chosen to avoid, to the extent possible, the development of resistance, such as by using compounds having different mechanisms of action, or, less preferably, using a bacteriostatic compound rather than a bacteriocidal compound.

DETAILED DESCRIPTION OF SPECIFIC EMBODIMENTS

Figure 1A:
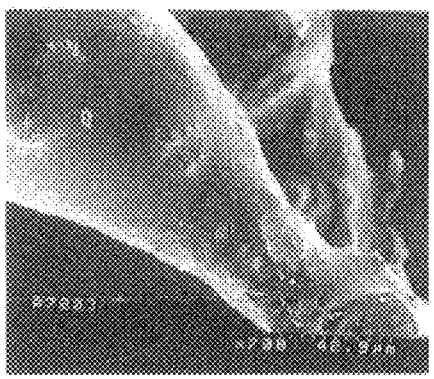
FIGS. 1A–1C depict SEM photomicrographs of various pads after challenge with bacteria and incubated.
Figure 1A:
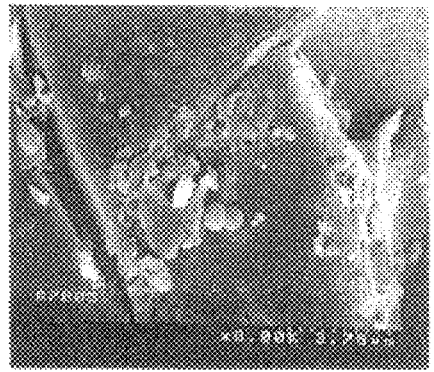

Nonwoven pads and similar articles are per se well-known and will not be discussed herein in detail. In general, the nonwoven articles of this invention are preferably made from a durable, synthetic fiber such as a polyamide, a polyester, or a tough polyolefin; exemplary preferable fibers are comprised of nylon 6/6, poly(ethylene terephthalate), or polypropylene. The raw material fibers preferably have a denier in the range of 6–200 dpf, with 15±2 dpf most preferred. The fibers are preferably provided from the manufacturer as staple fibers, preferably of 1.5"±0.5" lengths, already crimped (5–15 crimps/inch). The fibers should have a tenacity sufficient for domestic scrubbing applications; a fiber having a tenacity of at least about 2.5 gpd and an elongation of 100–175% is suitable for practicing this invention. The fibers provided by the manufacturer typically are providing having an antistatic finish thereon.

The fibers are typically provided by the manufacturer (e.g., DuPont, Wellman) as a bale, which is opened with a conventional device that gently opens the bale and separates the fibers from each other (e.g., similar to a carding device). The fibers are then formed into a thin web using a conventional device (e.g., a garnet). The thin web is then operated upon by a conventional cross-lapping device. Following this, the web is fed into a Rando Web device, which randomly redistributes the fibers in the web. The integrity of the web is then increased by an operation such as needlepunching. The result of this processing is a nonwoven article having a thickness of about 9.5 mm±3 mm (3/8"±1/8") and a base weight of about 4 oz./yd.$^2$ (about 136 g/m$^2$).

The patent described in the Background section, the disclosures of which are incorporated herein by reference, are typically suitable for use in the present invention.

The fibers of the nonwoven article are then permanently coated with a mixture of antimicrobial compounds. Preferably, the antimicrobial compounds are dispersed in a curable liquid that is coated onto the fibers of the nonwoven and then cured, although two or more coating operations can be performed with differing antimicrobials. The fibers also can be coated prior to formation of the web if an abrasive (as described later) is not present in the coating formulation (because the abrasive fibers would likely cause significant wearing of the fiber handling equipment). Suitable antimicrobial compounds should have limited solubility in water so that they do not leach from the coating in use (or afterwards while the pad is still wet), they should have a low toxicity in the event they do leach out (and for safety of the workers making the product), and should be hypoallergenic to the extent possible (e.g., non-dermally irritating).

One class of exemplary antimicrobials are iodosulfones such as diiodomethyl p-tolyl sulfone (CAS Reg. No. 20018-09-1), diiodomethyl p-chlorophenyl sulfone (CAS Reg. No. 20018-12-6), and the like, and mixtures thereof; these sulfones are known by their respective trademarks of AMICAL 48 and AMICAL 77; AMICAL FLOWABLE (EPA Reg. No. 48301-24, from Angus Chem. Co.) is preferred. Antimicrobials are preferably chosen also for their specificity against certain bacteria known (and/or suspected) to cause foodborne illness. Other antimicrobials include urea compounds such as imidazolidinyl urea and diazolidinyl urea, butylcarbamates such as iodopropynyl butylcarbamate.

Another class of suitable compounds not typically identified as antimicrobials include detergents that are capable of lysing cells, such as alkali alkyl sulfates, such as sodium lauryl sulfate or the like, wherein the cation is typically sodium or potassium, and the alkyl group has eight to 20 carbon atoms. Other suitable compounds include triclosan, quarternary anunonium compounds, and other disinfectants.

The antimicrobial is coated onto the fibers of the nonwoven article preferably by being dispersed in a curable, film-formable vehicle or binder. Suitable binders can be those typically used in nonwoven abrasives, such as phenol formaldehyde, acrylic latex, and styrene butadiene latex. These binders are typically provided by their manufacturers as aqueous liquids. The antimicrobial compound must be dispersible in the binder, either directly or with the aid of a compatible surfactant or coupling agent that does not degrade the antimicrobial properties of the biocide or interfere with coating the fibers or curing of the coating. Because these types of binders (aqueous-based, latexes) are typically provided as a liquid, the antimicrobial can be compounded with the binder under low shear to form a liquid binder/antimicrobial mixture. Although any suitable method for mixing will likely function, it is preferred to mix under low shear (such as with a paddle mixer). The inder is preferably thermally-curable at a relatively low temperature, most preferably at a temperature in the range of 250° F.±25° F.; the curing temperature must be below the temperature at which the antimicrobial degrades or decomposes. To facilitate curing at the relatively low temperature range indicated, a cross-linking agent is preferably added to the binder composition. Suitable cross-linking agents are various bifunctional and multifunctional aziridines such as described in U.S. Pat. Nos. 3,874,914, 4,278,578, 4,031,053, 4,605,698, 5,300,325, 5,164,467, and 5,545,713 (the disclosures of which are incorporated herein by reference). Additionally, the binder must have an affinity for the fibers of the nonwoven so that the binder in a liquid form will wet and coat (i.e., form a film on) the fibers and remain coated until curing is achieved. Further, the binder in a cured state should be sufficiently flexible, as is the pad, so that it does not crack or degrade during use.

The nonwoven article is coated with the binder/antimicrobial mixture. Preferably the fibers of the nonwoven are coated by spraying the binder/antimicrobial mixture onto the nonwoven until it is saturated; dipping in a bath can also be used. Thereafter, the binder is cured in an oven to form an antimicrobial coating on the fibers of the nonwoven. The coating and curing processes is repeated preferably about 4 times per article to produce a commercial product. The total amount of binder coated onto the fibers will be determined, to a significant extent, by the characteristics desired for the final product. In general, the more binder the higher the production and materials cost, the more efficient the antimicrobial properties (i.e., there are fewer uncoated areas of the nonwoven), and the more durable the product (i.e., the thicker the coating the more wear-resistant it is likely to be). The amount of binder (with the admixed antimicrobial and other ingredients) coated and cured onto the nonwoven can be determined by weighing the nonwoven before and after coating and curing. As mentioned above, the preferred basis weight for the present nonwoven before being coated is about 4 oz./yd.$^2$. After four rounds of coating and curing, the preferred basis weight is 8–60 oz./yd.$^2$, most preferably about 21 oz./yd.$^2$.

After the coating is subjected to a final curing step, the nonwoven is stored in the configuration of a roll until such time as it is used to make a commercial product. At that time, the roll is unwound and cut into rectangular pads that are packaged and shipped to retail establishments for purchase and use by the consumer.

The binder preferably also has additional ingredients compounded therein along with the antimicrobials. One preferred ingredient is abrasive particles, especially alumina having a size distribution generally between −120 mesh and +240 mesh or finer (e.g., 65–110 μm or finer). Alumina (aluminum oxide) is a preferred abrasive material because it is relatively inexpensive; other suitable abrasives include silicates such as silica (silicon oxide) and magnesium silicate, carbides such as silicon carbide and tungsten carbide, and any other conventional abrasive available in a particulate form that is suitable for the final application and can be dispersed in the liquid binder. (For example, a very hard abrasive would likely not be suitable for household use where soft plastic surfaces, such as FORMICA brand polymers (urea-formaldehyde and melamine), are the substrates to be cleaned and scrubbed, or anywhere the appearance of the substrate might be compromised by the use of too aggressive an abrasive.)

Other ingredients that can be compounded into the binder are colorants (e.g., dyes or pigments, such as phthalocyanine green), processing aids, flow control agents, antioxidants, and the like.

Figure 1B:
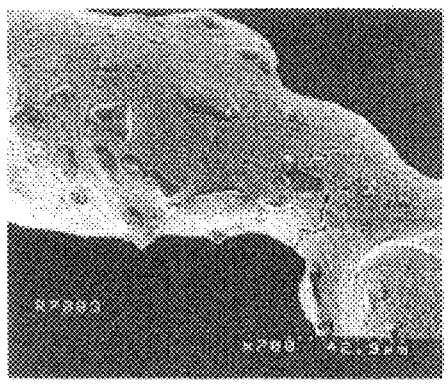
Figure 1B:
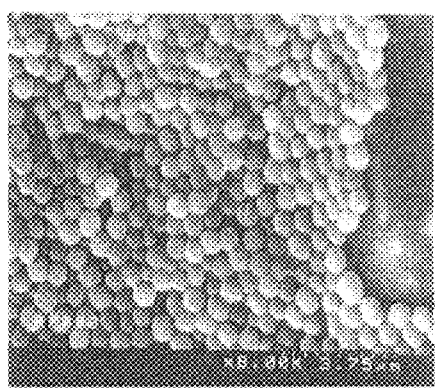
Figure 1C:
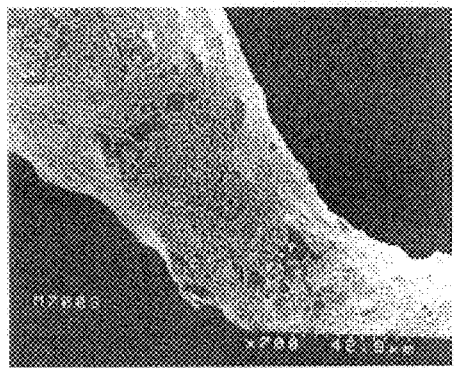
Figure 1C:
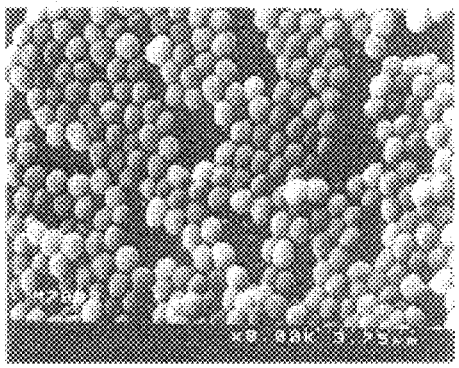

Pads were made according to this invention, although some were made without an antimicrobial mixture in the coating. FIGS. 1A through 1C depict SEM photomicrographs of these pads challenged with a combination of *Staphylococcus aureus* (e.g., ATCC 6538) and *Salmonella choleraesuis* (e.g., ATCC 10708), and incubated for 24 hours. FIG. 1A shows a pad according to this invention with an antimicrobial mixture of AMICAL and sodium lauryl sulfate after challenge and incubation, where it is seen that there are virtually no bacteria present; the 8000× magnification on the right hand side shows two bacteria. FIG. 1B depicts a similar pad made without the antimicrobial mixture, and FIG. 1C depicts a conventional, commercially available pad (3M Company) after challenge and incubation, where it is seen that there is significant bacterial growth.

Figure 2A:
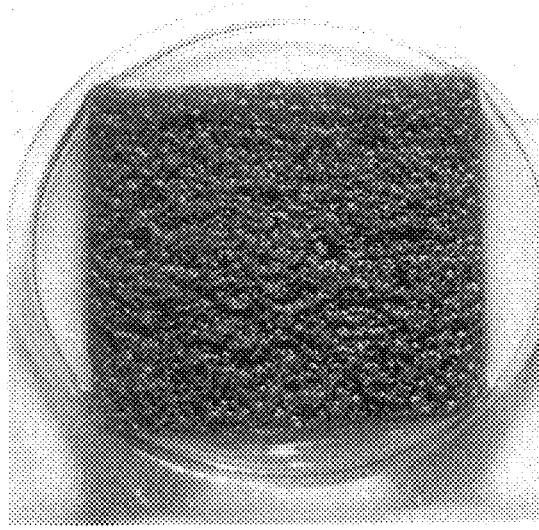
FIGS. 2A–2B depict photographs of two pads after challenge with bacteria and incubated.
Figure 2B:
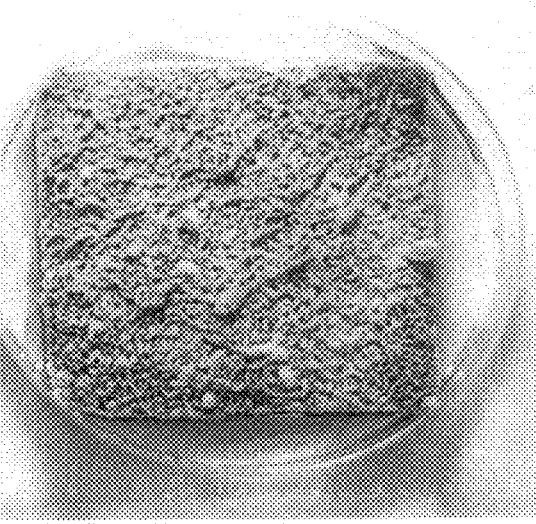

FIGS. 2A and 2B are color photographs of a pad according to this invention with an AMICAL and sodium lauryl sulfate mixture in the coating (2 A) and without the antimicrobial mixture (2 B). Both pads were challenged with the bacteria mixture used for the challenge shown in FIGS. 1A–1C and incubated for 24 hours. It is clearly seen that there is significant growth on the pad without the antimicrobial mixture.

The benefits of the present invention are that the abrasive pad produced is resistant to the growth of bacteria even when residual water remains in the pad. As mentioned above, the presence of water is often sufficient to allow the growth of undesirable microbes. While this problem is more apparent with absorbent articles such as sponges and towels, the problem is generally unappreciated with nonabsorbent articles such as nonwoven scrubbing pads. The present invention solves this problem by anchoring an antimicrobial agent in a binder that coats the fibers of the nonwoven.

Use of an antimicrobial anchored to the pad also, to a certain extent, helps to prevent resistance. Spreading a cleaning product containing antimicrobial on kitchen surface areas (e.g., using a spray on a kitchen counter) will necessarily result in some dilution of the product and the antimicrobial and non-uniform application of the product, leading to incomplete elimination of bacteria and thus fostering resistance. With this invention, the antimicrobial compounds are anchored to the pad and will have a high and uniform concentration of the compounds on the surface of the pad. Thus, with this invention the concentration of the antimicrobials is constant, and the use of two antimicrobials, preferably having different modes of action, diminishes the factors likely to promote bacterial resistance.

The foregoing description is meant to be illustrative and not limiting. Various changes, modifications, and additions may become apparent to the skilled artisan upon a perusal of this specification, and such are meant to be within the scope and spirit of the invention as defined by the claims.

What is claimed is:

1. A non-absorbent, abrasive scrubbing pad comprising:
   A. a nonwoven pad of synthetic fibers; and
   B. a cured polymeric coating on the fibers of the nonwoven pad, said coating comprising (i) a mixture of antimicrobial compounds and (ii) abrasive particles, said antimicrobial compounds (i) and abrasive particles (ii) being present when said coating is cured and thereby being bound therein.

2. The scrubbing pad of claim 1, wherein the fibers are selected from the group consisting of polyamides, polyesters, polyolefins, and mixtures thereof.

3. The scrubbing pad of claim 2, wherein the fibers are selected from the group consisting of nylons, poly(ethylene terephthalate), and polypropylene.

4. The scrubbing pad of claim 3, wherein the fibers are nylon.

5. The scrubbing pad of claim 1, wherein the coating is formed from a polymer selected from the group consisting of phenol-formaldehydes, acrylic latexes, and styrene butadiene latexes.

6. The scrubbing pad of claim 1, wherein the antimicrobial compound is a sulfone.

7. The scrubbing pad of claim 6, wherein one antimicrobial compound is selected from the group consisting of diidomethyl p-tolyl sulfone, diiodomethyl p-chlorophenyl sulfone, and mixtures thereof.

8. The scrubbing pad of claim 1, wherein one antimicrobial compound is an alkali alkyl sulfate.

9. The scrubbing pad of claim 8, wherein said compound is sodium lauryl sulfate.

10. The scrubbing pad of claim 1, wherein the abrasive particles are selected from the group consisting of alumina, silica, magnesium silicate, and silicon carbide.

11. The scrubbing pad of claim 10, wherein the abrasive particles are alumina.

12. A method for making a non-absorbent, antimicrobial, abrasive scrubbing pad, comprising the steps of:
   A. providing a nonwoven web comprising hydrophobic synthetic fibers;
   B. providing a liquid, film-formable binder effective to coat the synthetic fibers in the nonwoven web;
   C. providing (i) a mixture of at least two antimicrobial compounds having limited solubility in water and (ii) abrasive particles;
   D. admixing the antimicrobial compounds and the abrasive particles with the binder to produce a binder mix;
   E. coating the fibers of the nonwoven web with the binder mix, curing the binder, and repeating the coating and curing as desired; and
   F. cutting the coated, nonwoven web into a scrubbing pad.

13. The method of claim 12, wherein the synthetic fibers are selected from the group consisting of polyamides, polyesters, polyolefins, and mixtures thereof.

14. The method of claim 13, wherein the fibers are selected from the group consisting of nylons, poly(ethylene terephthalate), and polypropylene.

15. The method of claim 12, wherein the coating is formed from a polymer selected from the group consisting of phenol-formaldehydes, acrylic latexes, and styrene butadiene latexes.

16. The method of claim 12, wherein one of said antimicrobial compounds is a sulfone.

17. The method of claim 16, wherein said antimicrobial compound is selected from the group consisting of diidomethyl p-tolyl sulfone, diiodomethyl p-chlorophenyl sulfone, and mixtures thereof.

18. The scrubbing pad of claim 7, wherein one antimicrobial compound is an alkali alkyl sulfate.

19. The scrubbing pad of claim 18, wherein said compound is sodium lauryl sulfate.

20. The method of claim 12, wherein the abrasive particles are selected from the group consisting of alumina, silica, magnesium silicate, and silicon carbide.

21. The method of claim 16, wherein the abrasive particles are alumina.

22. The pad of claim 1, wherein the mixture of antimicrobial compounds comprises sodium lauryl sulfate and at least one compound selected from the group consisting of diidomethyl p-tolyl sulfone, diiodomethyl p-chlorophenyl sulfone, and mixtures thereof.

23. The method of claim 12, wherein the mixture of antimicrobial compounds comprises sodium lauryl sulfate and at least one compound selected from the group consisting of diidomethyl p-tolyl sulfone, diiodomethyl p-chlorophenyl sulfone, and mixtures thereof.

* * * * *